(12) United States Patent
Tyrrell (10) Patent No.: US 6,406,919 B1
(45) Date of Patent: Jun. 18, 2002

(54) WHOLE BLOOD COLLECTION DEVICE AND METHOD

(75) Inventor: Steven P. Tyrrell, Highland Park, IL (US)

(73) Assignee: BioSafe Laboratories, Inc., Chicago, IL (US)

( * ) Notice: Subject to any disclaimer, the term of this patent is extended or adjusted under 35 U.S.C. 154(b) by 0 days.

(21) Appl. No.: 09/464,757

(22) Filed: Dec. 16, 1999

(51) Int. Cl.[7] ................................................ G01N 1/00
(52) U.S. Cl. ........................ 436/174; 436/169; 436/179; 436/180; 422/99; 422/102; 422/58; 600/573
(58) Field of Search .................... 436/63, 174, 176, 436/177, 179, 180, 164, 169; 422/99, 102, 58, 61; 435/287.3, 288.4, 288.5; 600/573, 577, 578

(56) References Cited

U.S. PATENT DOCUMENTS

| | | | |
|---|---|---|---|
| 3,640,267 A | 2/1972 | Hurtig et al. | 600/578 |
| 4,378,333 A | 3/1983 | Laipply | 422/100 |
| 4,957,582 A | 9/1990 | Columbus | 156/332 |
| 5,163,442 A | 11/1992 | Ono | 600/573 |
| 5,200,152 A | 4/1993 | Brown | 422/102 |
| 5,310,523 A | 5/1994 | Smethers et al. | 422/57 |
| 5,503,803 A | 4/1996 | Brown | 422/102 |
| 5,638,828 A | * 6/1997 | Lauks et al. | 600/573 |
| 5,651,766 A | * 7/1997 | Kingsley et al. | 604/6.04 |
| 5,674,457 A | 10/1997 | Williamsson et al. | 422/102 |
| 5,824,268 A | * 10/1998 | Bernstein et al. | 422/56 |
| 6,036,659 A | * 3/2000 | Ray et al. | 600/573 |

FOREIGN PATENT DOCUMENTS

| WO | 79/01131 | * 12/1979 |
|---|---|---|
| WO | WO 99/57559 | 11/1999 |

* cited by examiner

Primary Examiner—Maureen M. Wallenhorst
(74) Attorney, Agent, or Firm—Olson & Hierl, Ltd.

(57) ABSTRACT

A system for collecting whole blood includes a metering chamber and a reservoir. A movable gasket or seal is positioned to a fill position, and whole blood is added to the metering chamber until the metering chamber is full. Then the gasket is moved to a closed position, thereby moving blood from the metering chamber to the reservoir and sealing the reservoir. A diluting liquid contained in the reservoir is mixed with the whole blood to dilute and stabilize the whole blood in the reservoir for later analysis of one or more selected blood components.

34 Claims, 10 Drawing Sheets

WHOLE BLOOD COLLECTION DEVICE AND METHOD

BACKGROUND

The present invention relates to a collection device and method that allow whole blood to be collected precisely and reliably at a remote site and then shipped to a central laboratory for analysis.

In the past, it has been common practice to ask an individual to come to a laboratory or office to have whole blood drawn for analysis. This represents a substantial inconvenience to the individual. A need presently exists for an improved system that overcomes this inefficiency.

SUMMARY

The preferred embodiment described below is designed to collect a precisely metered volume of whole blood without the need for training, and without the need for the user to perform complex techniques. The system automatically dilutes the whole blood and seals the diluted blood in the device when the user simply turns a lever. By diluting blood in the field, blood stability is improved. Blood dilution also improves the likelihood that the analyzing laboratory will have an adequate physical sample of liquid with which to work, once the specimen reaches the laboratory for analysis. If desired, a stabilizing composition can be placed in the diluting liquid to stabilize specific blood components prior to analysis.

This section is intended only by way of introduction, and it should not be used to limit the scope of the following claims.

DETAILED DESCRIPTION OF THE PRESENTLY PREFERRED EMBODIMENTS

Figure 1:
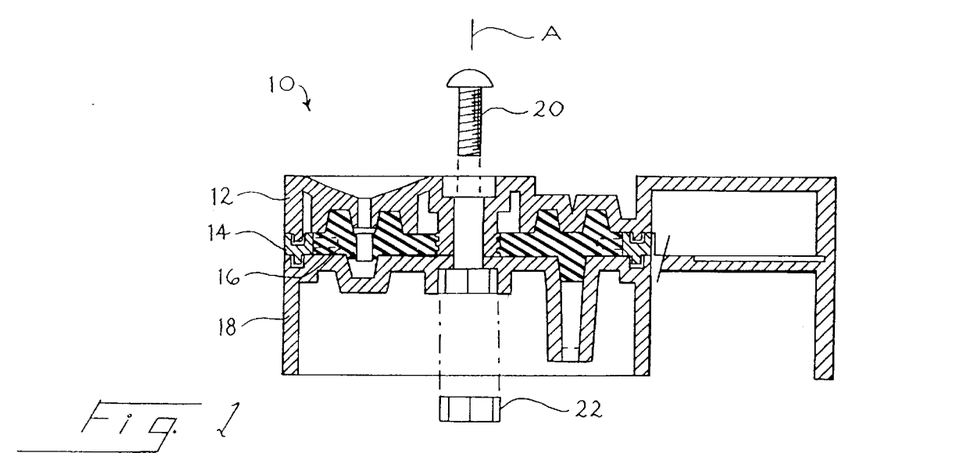
FIG. 1 is a cross-sectional view of a blood collection device that incorporates a preferred embodiment of the present invention.
Figure 2:
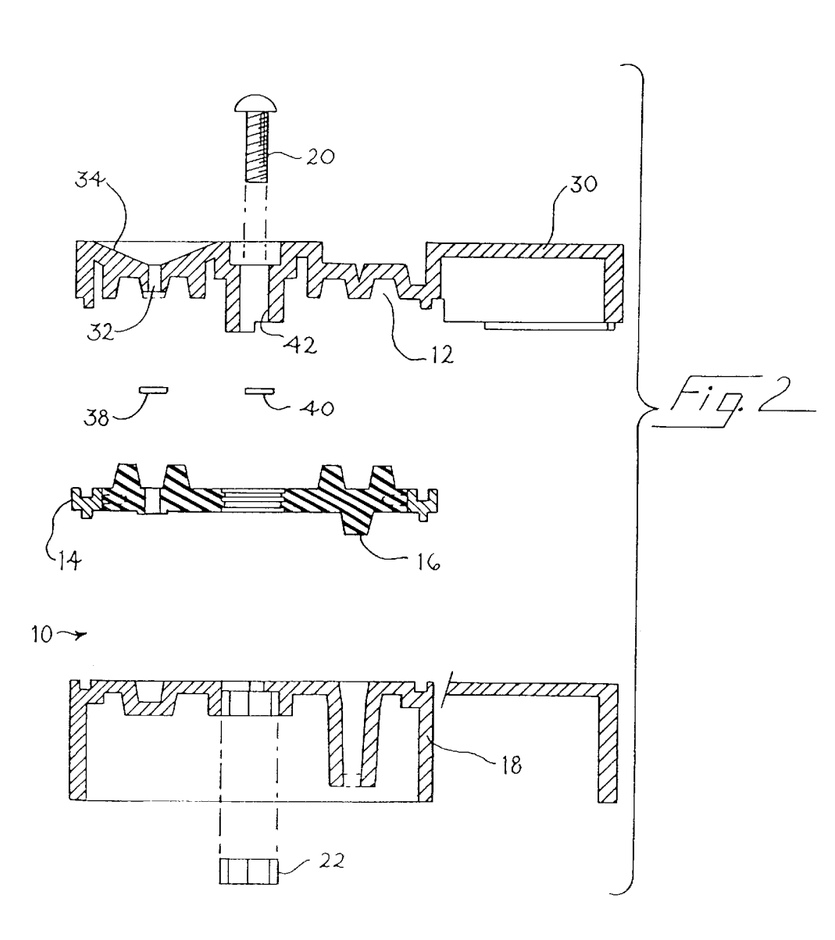
FIG. 2 is an exploded view of the device of FIG. 1.
Figure 3:
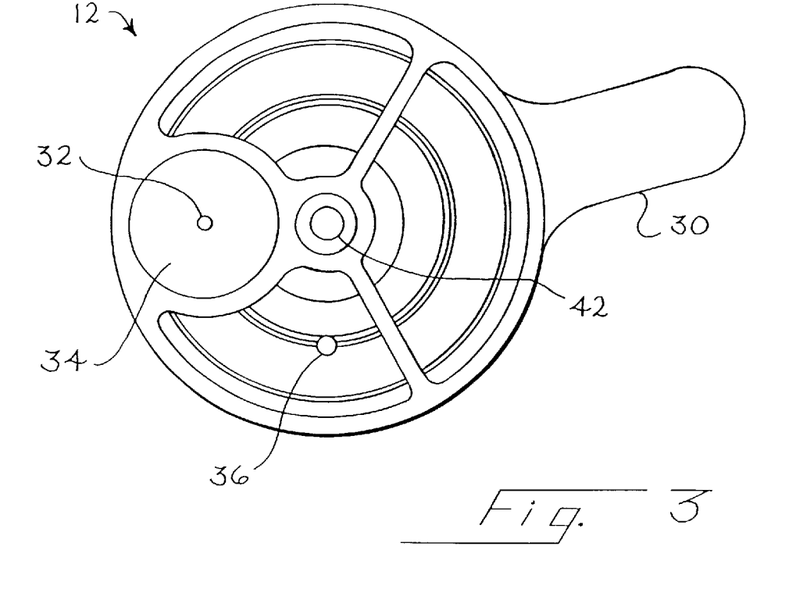
FIGS. 3, 4, 5 and 6 are top, bottom, upper perspective and lower perspective views, respectively, of an upper plate included in the device of FIG. 1.

Turning now to the drawings, FIG. 1 shows a cross-sectional view of a whole blood collection device 10 that incorporates a preferred embodiment of this invention. The device 10 is a small, disposable device that has been designed for use by an untrained individual to collect a small volume of whole blood for later analysis. The device 10 includes an upper plate 12, a middle plate 14 that supports a gasket 16, and a lower plate 18. The device 10 is held together by a screw 20 and a nut 22. The screw 20 defines an axis of rotation A, and the middle plate 14 and the gasket 16 are mounted for rotation about the axis A as described below. FIG. 2 provides an exploded cross-sectional view of the elements of FIG. 1.

Figure 4:
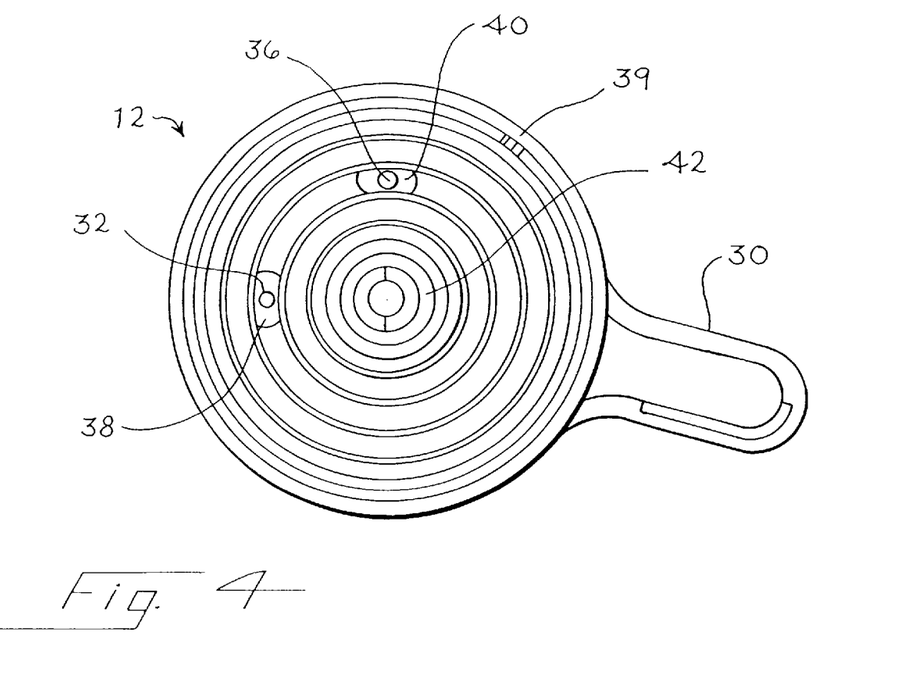
Figure 5:
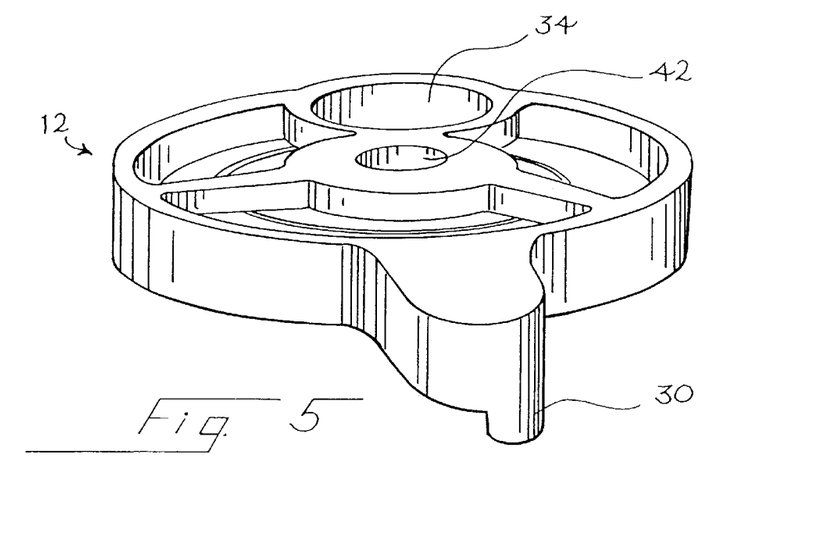
Figure 6:
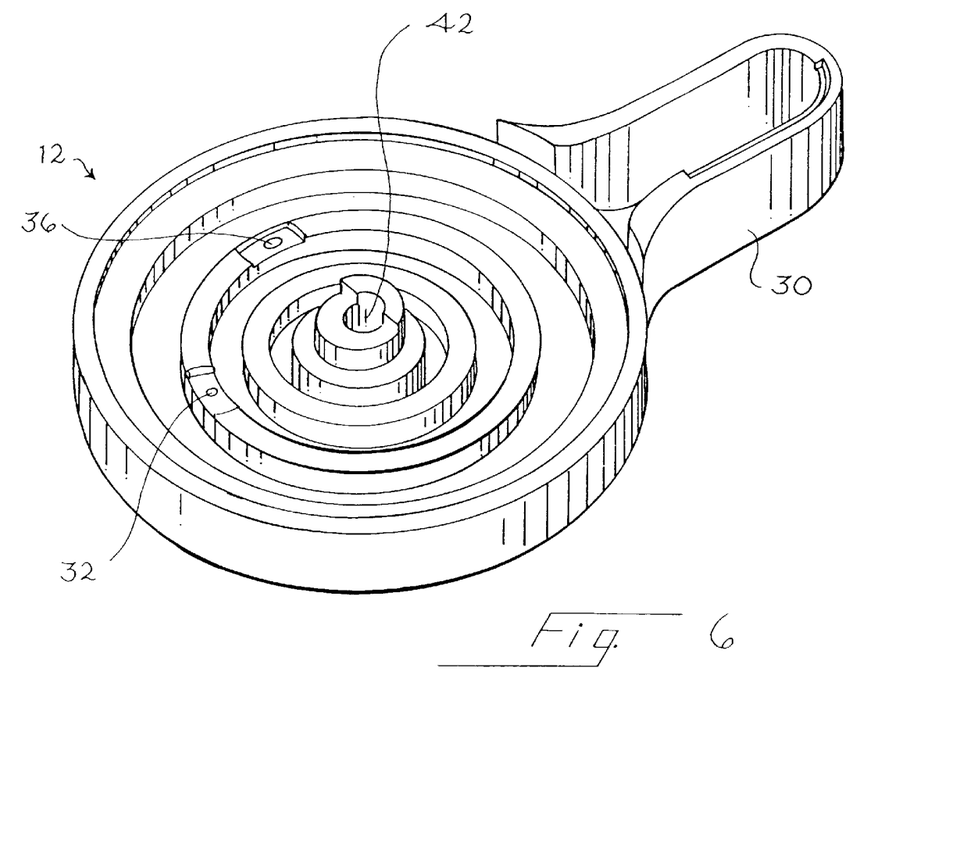

As best shown in FIGS. 2–6, the upper plate 12 includes a radially extending handle 30. The upper plate 12 also defines a fill port 32 and a view port 36, both of which extend completely through the upper plate 12, as well as a funnel 34 surrounding the fill port 32. An anticoagulant pad 38 is mounted under the fill port 32, and a view port pad 40 is mounted under the view port 36. The pad 38 is a porous sheet impregnated with an anticoagulant. Blood passing through the fill port 32 mixes with this anticoagulant as it passes through the pad 38. The upper plate 12 also defines a central opening 42 centered around the axis A, and the lower surface of the upper plate 12 includes a latching element 39 (FIG. 4).

Figures 7, 8:
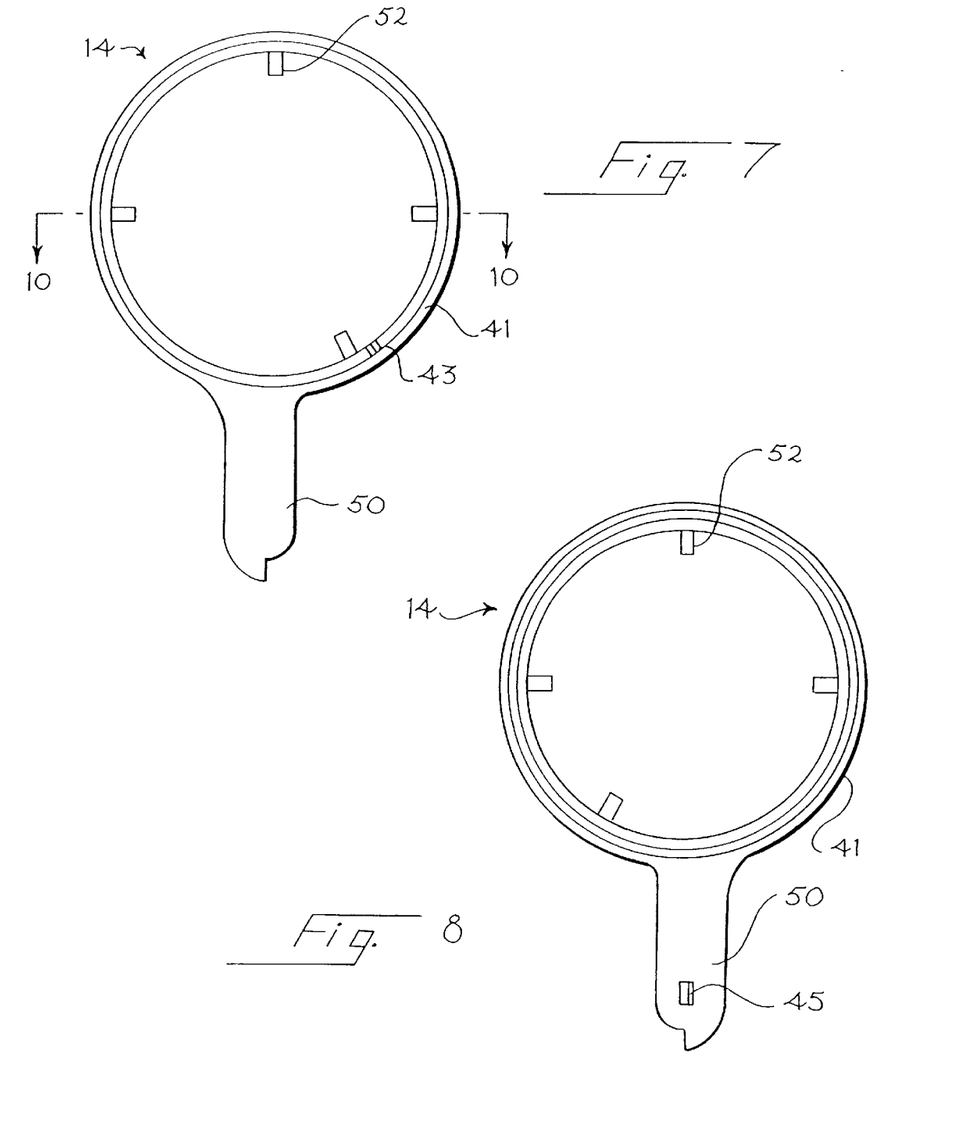
FIGS. 7, 8 and 9 are top, bottom, and upper perspective views, respectively, of a middle plate included in the device of FIG. 1.
Figure 9:
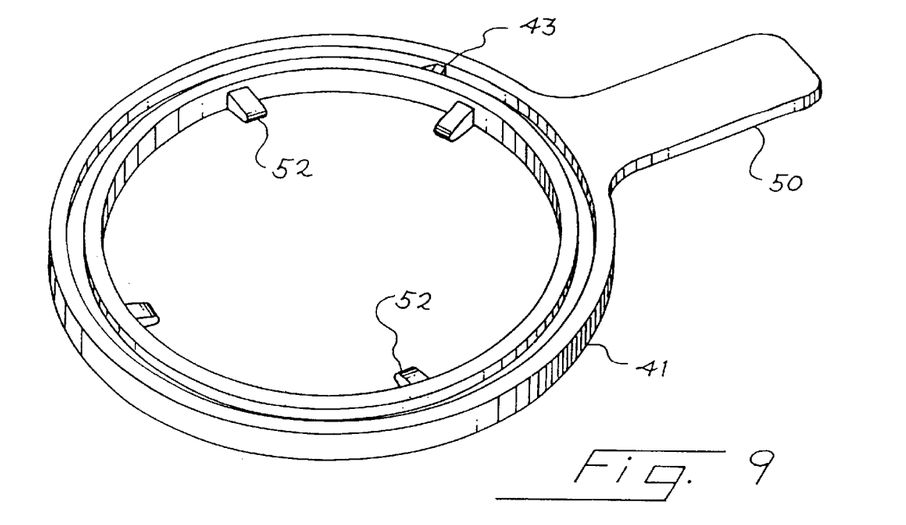
Figure 10:
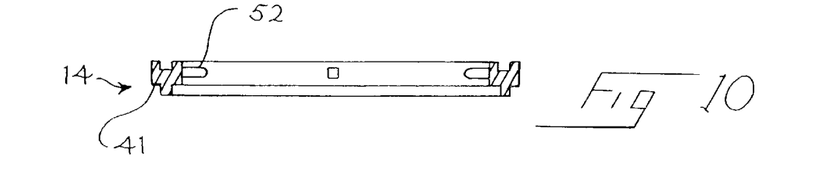
FIG. 10 is a cross-sectional view taken along line 10—10 of FIG. 7.
Figure 11:
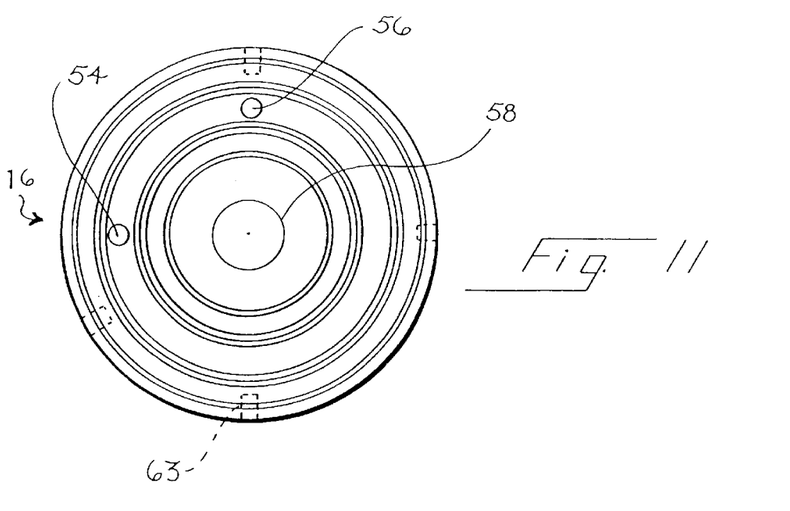
FIGS. 11, 12, 13 and 14 are top, bottom, upper perspective and lower perspective views, respectively, of a gasket adapted for mounting to the middle plate of FIGS. 7 through 10.

As best shown in FIGS. 7, 8 and 9, the middle plate 14 includes a circular rim 41 that supports a radially extending handle 50 and inwardly extending tabs 52. The tabs 52 secure the gasket 16 to the middle plate 14 and prevent relative movement therebetween. A first latching element 43 (in this case in the form of a ramp) is positioned on the upper side of the rim 41. A second latching element 45 (in this case also in the form of a ramp) is formed in the lower face of the handle 50.

As best shown in FIGS. 11–14, the gasket 16 includes a fill port through hole 54 and a view port through hole 56 that are positioned to align with the fill port 32 and the view port 36, respectively, of the upper plate 12 when the middle plate 14 and the gasket 16 are positioned in a fill position. The gasket 16 also defines a central opening 58 sized to receive the screw of FIG. 1.

Figure 12:
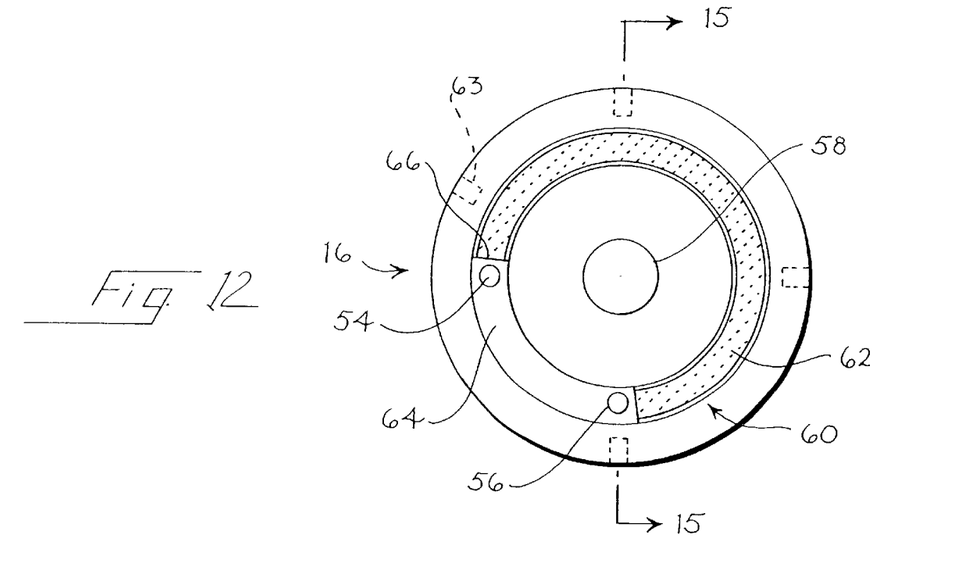
Figure 13:
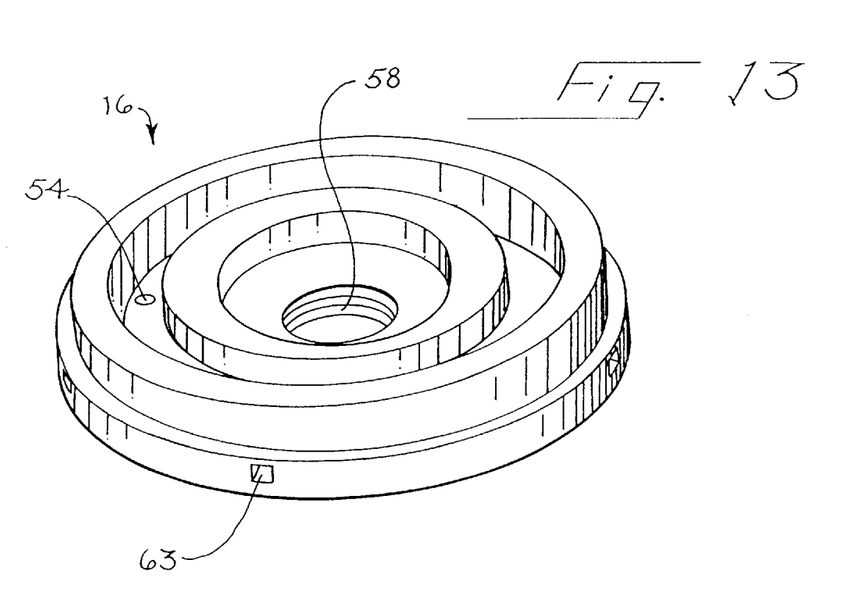
Figure 14:
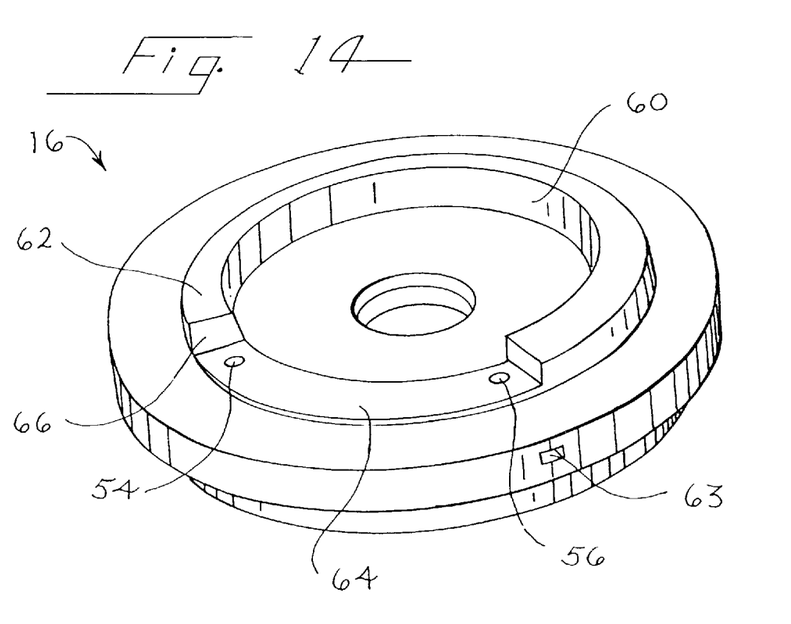
Figure 15:
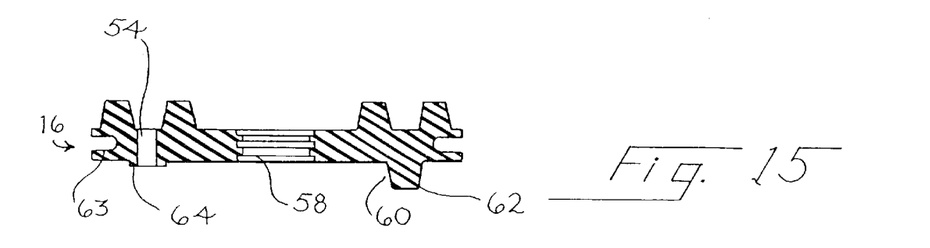
FIG. 15 is a cross-sectional view taken along line 15—15 of FIG. 12.
Figure 16:
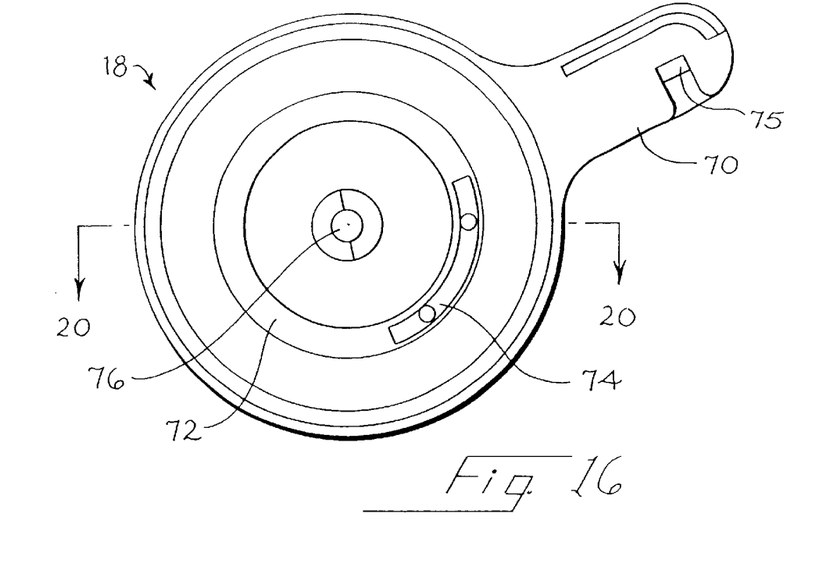
FIGS. 16, 17, 18 and 19 are top, bottom, upper perspective and lower perspective views, respectively, of a lower plate included in the device of FIG. 1.

A protruding element 60 extends from the lower surface of the gasket 16. This protruding element 60 is annular in shape, and it includes two separate portions 62, 64. The first portion 62 extends over an arc of about 245 degrees, as shown in FIG. 12, and it extends substantially away from the plane of the gasket 16, as shown in FIG. 15. The second portion 64 of the protruding element 60 extends over an arc of about 115 degrees (FIG. 12) and extends only a small distance beyond the lower surface of the gasket 16 (FIG. 15). As shown in FIG. 12, the through holes 54, 56 are formed in the second portion 64 of the protruding element 60. A leading portion of the first portion 62 of the protruding element 60 acts as a sweeping element 66, as described in detail below. Recesses 63 are positioned to receive the tabs 52 of the middle plate 14 (FIGS. 7–9).

Figure 20:
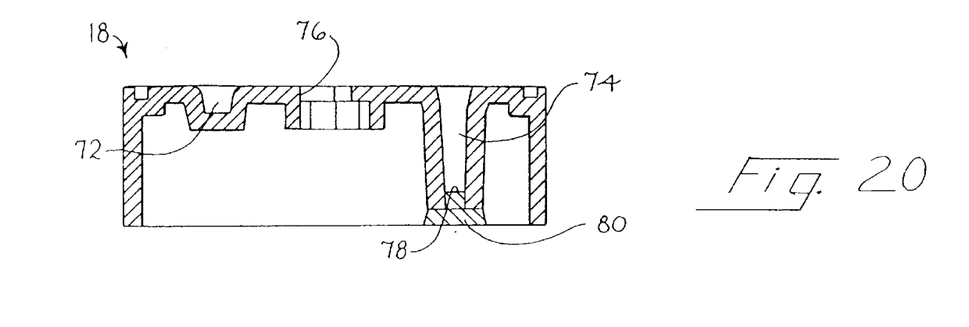
FIG. 20 is a cross-sectional view taken along line 20—20 of FIG. 16.

FIGS. 16–20 provide further information regarding the construction of the lower plate 18, which includes a handle 70 that extends radially away from a central opening 76. An annular capillary channel 72 is formed in the upper surface of the lower plate 18, concentrically with the central opening 76. As shown in FIG. 20, the capillary channel 72 has a relatively shallow depth. In this embodiment the sidewalls of the capillary channel 72 each diverge by an included angle of about 10 degrees with respect to a line drawn perpendicularly to the upper surface of the lower plate 18. The capillary channel 72 is sized to receive and be sealed by the first portion 62 of the protruding element 60 of the gasket 16 (FIGS. 11–14).

The capillary channel 72 empties at both ends into a reservoir 74 that is also concentric with the central opening 76. As shown in FIG. 20, the reservoir 74 is substantially deeper than the capillary channel 72, and two access ports 78 are formed in the bottom of the reservoir 74, sealed by a plug 80. The upper face of the handle 70 supports a latching element 75.

The latching elements 39, 75 on the upper and lower plates 12, 18, respectively, cooperate with mating latching elements 43, 45 on the middle plate 14 to form a snap latch. The snap latch holds the handle 50 inside a recess formed by the handles 30, 70 once the middle plate 14 has been moved to the closed position described below.

The operation of the device 10 described above will now be explained with reference to FIGS. 21–24. As shown at block 100 of FIG. 24, the device 10 is provided to a user, such as an individual desiring to obtain a laboratory analysis of any suitable blood component. As selected examples, the device 10 can be used to obtain a complete blood count, and/or an analysis of blood lipids, thyroid stimulating hormone, or prostate specific antigen. Other blood components can also be analyzed.

Figures 21, 22, 23:
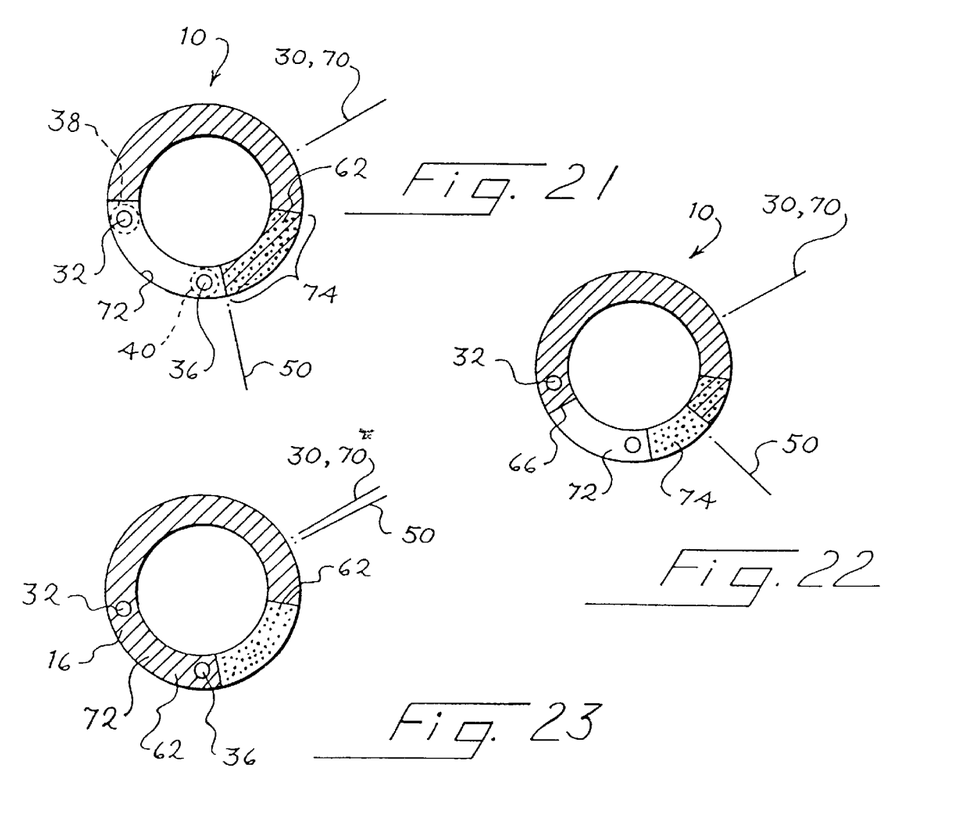
FIGS. 21, 22 and 23 are schematic views of selected elements of the device of FIG. 1 in fill, intermediate, and closed positions, respectively.

In its initial configuration, the collection device 10 is positioned with the middle plate 14 and the gasket 16 in the fill position shown in FIG. 21. In the fill position both the fill port 32 and the view port 36 are aligned with the corresponding openings in the gasket and with the capillary channel 72, and the capillary channel 72 is isolated from the reservoir 74 by the first portion 62 of the protruding element. In the fill position the handles 30, 70 and the handle 50 are positioned as schematically shown in FIG. 21.

Figure 24:
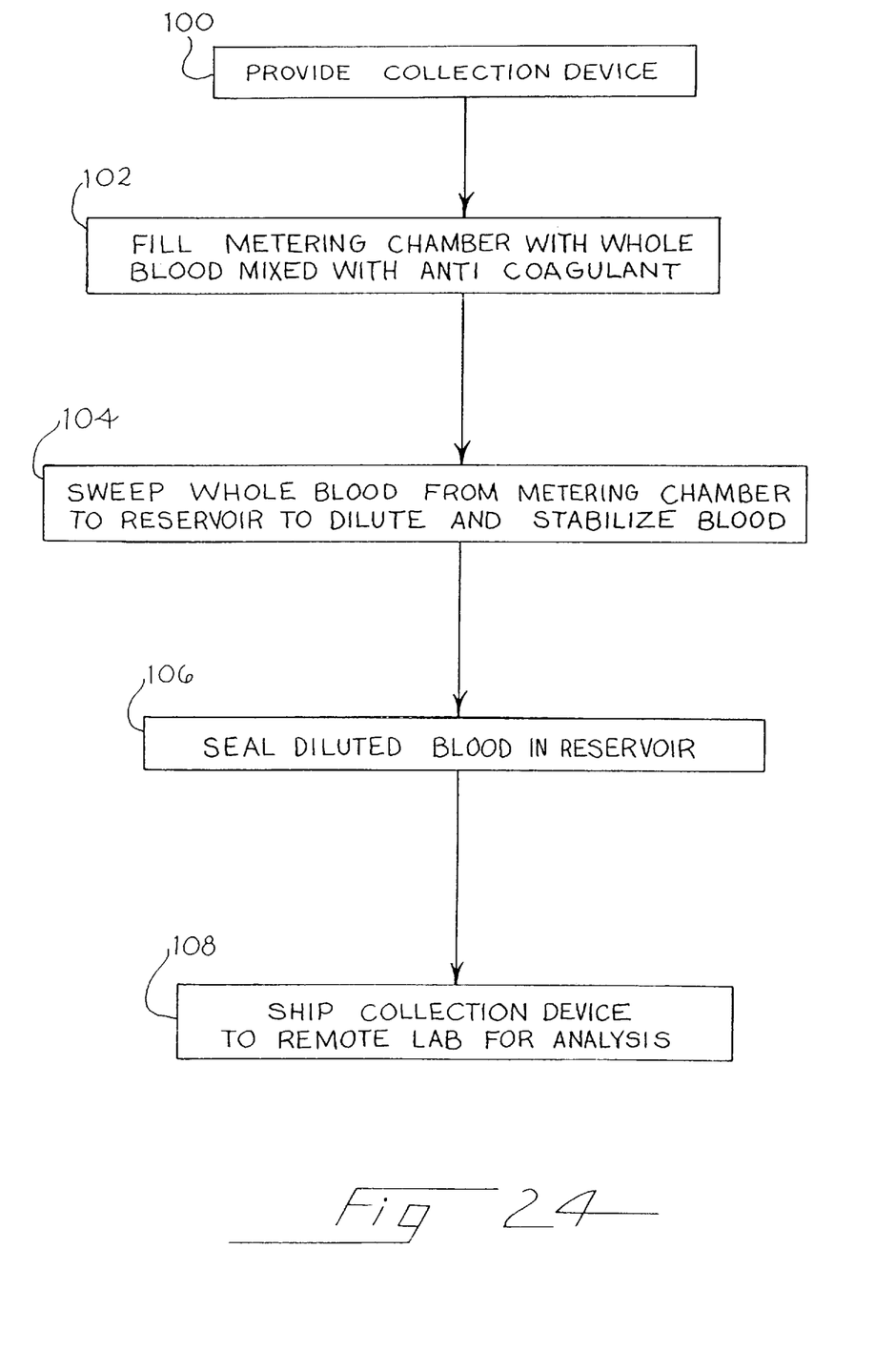
FIG. 24 is a flow chart of a method for collecting whole blood for remote analysis.

As shown in block 102 of FIG. 24, a metering chamber formed by the capillary channel 72 is then filled with whole blood mixed with anticoagulant. Blood, obtained for example with a finger stick, flows through the fill port 32 into the capillary channel 72. In so doing, the blood passes through the anticoagulant pad 38 located directly under the fill port 32. Blood wets and passes through the pad 38, causing anticoagulant chemicals to leach from the pad 38 and mix with the blood. In this way, premature blood clotting is prevented and blood is maintained in a liquid state until it mixes with the reagents in the reservoir 74.

After the capillary channel 72 is filled, blood flows upwardly toward the view port 36 and into contact with the porous plastic view port pad 40. After the pad 40 becomes saturated with blood, the view port 36 turns red, indicating to the user that the capillary channel 72 is full, and that the user can stop adding blood to the fill port 32.

The view port 36 does not turn red until the capillary channel 72 is completely filled with blood. In this way, the capillary channel 72 operates as a metering chamber. User-to-user differences in blood drop volume are taken into consideration, because the user continues to add blood to the device until the view port 36 turns red. In this way a precise volume of blood is collected in the capillary channel 72, in spite of differences among users.

As shown at 104 in FIG. 24, blood is then swept from the capillary channel 72 to the reservoir 74 to dilute and stabilize the blood. FIG. 22 schematically shows selected elements of the device 10 in an intermediate position between the fill position and the closed position. Note that the handle 50 has been rotated counterclockwise in a view of FIG. 22 to allow blood flow from the capillary channel 72 into the reservoir 74 and to seal the fill port 32. The sweeping element 66 acts as a squeegee to sweep blood out of the capillary channel 72 and into the reservoir 74. The handles 30, 70 can be grasped by the user to facilitate counterclockwise movement of the handle 50.

Figure 17:
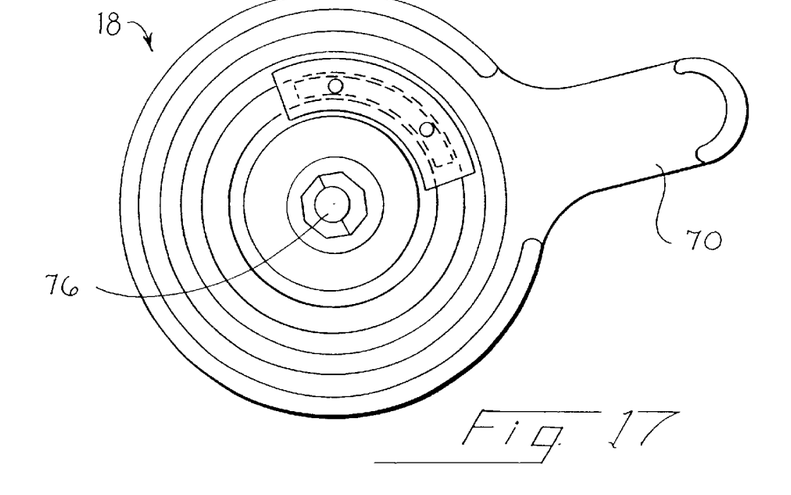
Figure 18:
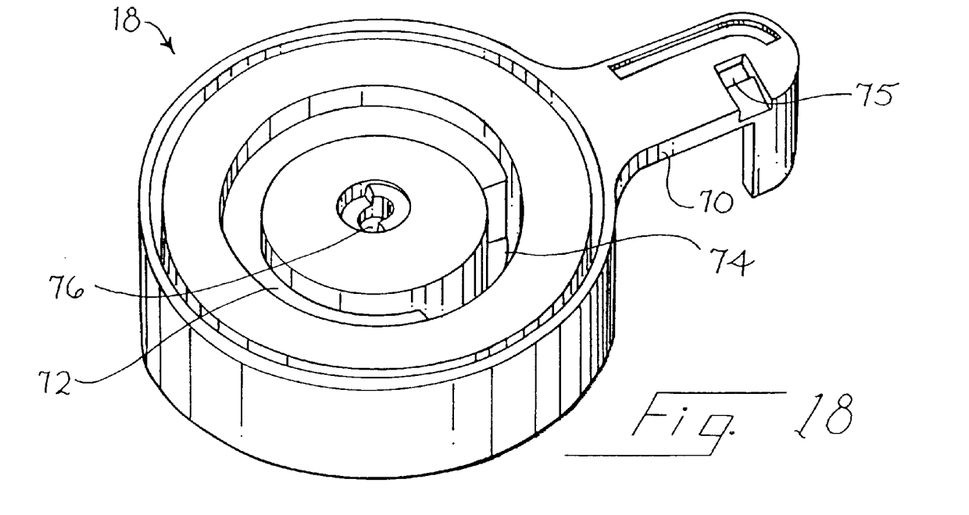
Figure 19:
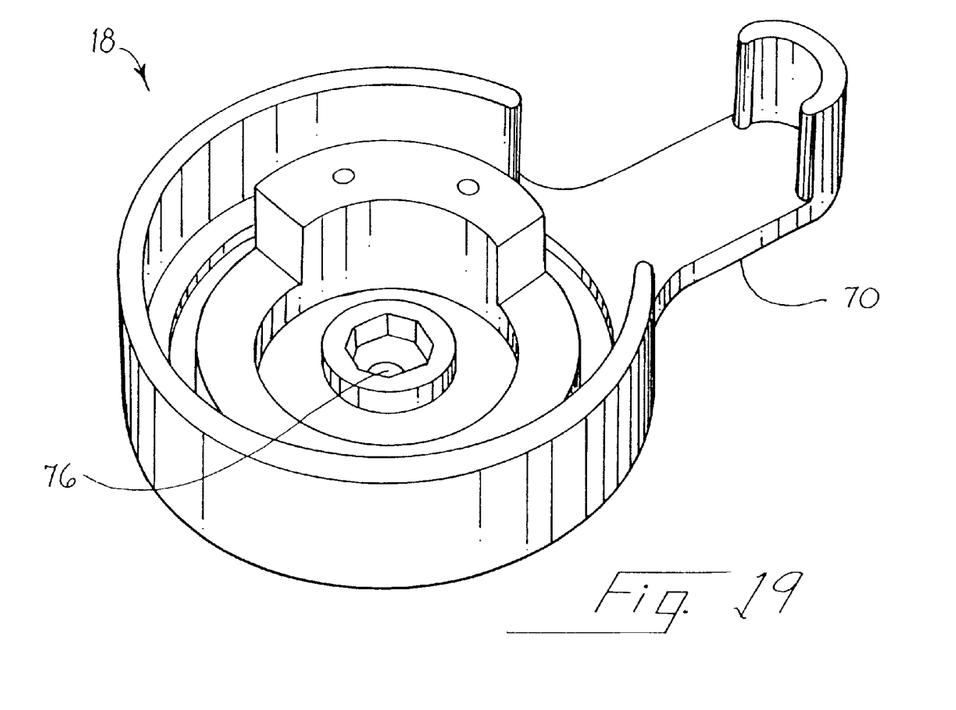

As shown at block 106 of FIG. 17, blood is then sealed in the reservoir 74. In this embodiment, the reservoir 74 initially contains a diluting liquid that optionally includes a blood stabilizing composition. The diluting liquid and the blood stabilizing composition can be inserted into the reservoir 74 via the access ports 78 before the plug 80 is applied.

As shown at FIG. 23, once the handle 50 is moved to the closed position, the first portion 62 of the protruding element 60 substantially fills the capillary channel 72 and seals and the reservoir 74 at both ends. The fill port 32 and the view port 36 are also closed by the gasket 16. In the closed position of FIG. 16, the handle 50 is aligned with the handles 30, 70, and the handle 50 is preferably held in the closed position by the latch described above. In this way the diluted blood is sealed in the reservoir for shipment.

As shown in block 108 of FIG. 24, the collection device is then shipped to a remote site for analysis. The device and the blood contained therein may be maintained at ambient temperature for storage and transport. The remote site of block 108 may be any site at which blood analysis can be performed, such as a hospital, a clinic, a pharmacy, or a suitably equipped home. Once the collection device 10 reaches the remote site, the diluted, stabilized whole blood is then removed from the reservoir 74 via the access ports 78 after the plug 80 has been removed.

The diluting liquid or diluent in the reservoir increases the liquid volume of the sample that is available for analysis. This facilitates analysis. The volume of diluting liquid in the reservoir is preferably at least as great as the volume of the metering chamber, and can be at least ten times as great as the volume of the metering chamber. Intermediate volumes of diluting liquid, where the volume of diluting liquid is at least three, six or nine times the volume of the metering chamber, can also be used.

Simply by way of example, and without intending any limitation, the following preferred dimensions and materials have been found suitable for use in one preferred embodiment.

DIMENSIONS TABLE

| Element | Preferred Dimensions |
|---|---|
| metering chamber width | 0.075 inch |
| metering chamber depth | 0.075 inch |
| metering chamber volume | 150 µL |
| reservoir volume | 900 µL |
| diluting liquid volume | 700 µL |

MATERIALS TABLE

| Element | Preferred Material |
|---|---|
| plates 12, 14, 18 | polyethylene |
| gasket 16 | styrene/ethylene/butylene polymer |
| anticoagulant pad 38 | polyethylene |

-continued

MATERIALS TABLE

| Element | Preferred Material |
| --- | --- |
| view port pad 40 | polyethylene |
| anticoagulant composition | EDTA |

The diluting liquid will vary widely, depending on the application. Suitable diluting liquids include the following examples:
1. EDTA, buffer, glucose, preservative, sodium chloride, stabilizers;
2. Citric acid, buffer, glucose, preservative, sodium chloride, stabilizers;
3. Formalin, ethanol, sodium chloride, stabilizers.

The preservatives of these examples may be any substance that inhibits bacterial or fungal growth, such as sodium azide, ProClin (a product of Supelco, Bellefonte, Pa.) or any number of other chemical agents. The stabilizers of these examples may be any substance designed to stabilize the analytical component of interest, such as sucrose and detergents (both ionic and nonionic). The buffers of these examples may be any component designed to stabilize the pH of the diluting liquid.

The preservative, buffer and stabilizer may or may not be included in the diluting liquid, depending on the intended use of the collected sample.

Of course, it should be understood that a wide range of changes and modifications can be made to the preferred embodiment described above. The gasket 16 operates as a seal, and in this embodiment the seal is formed in one piece. In an alternative embodiment, the seal may be formed from two or more sealing parts.

The preferred embodiment described above utilizes a rotary motion to sweep blood from the metering chamber into the reservoir. In alternative embodiments a linear motion can be used. Also, in some alternative embodiments blood is swept from the metering chamber into the reservoir by pneumatic pressure rather than the squeegee action described above. Additionally, the metering chamber may be larger than a capillary channel, and the reservoir may or may not contain a diluting liquid.

As used herein the term "position" is intended broadly to encompass a range of positions. For example, the intermediate position described above can correspond to any one of a range of positions.

The term "concentric" is intended broadly to encompass structure that extends over a full 360 degrees or all over only a fraction of 360 degrees.

The term "blood stabilizing composition" is intended broadly to encompass any composition for stabilizing one or more selected components of whole blood.

The foregoing detailed description has discussed only a few of the many forms that the present invention can take. For this reason, this detailed description is intended only by way of illustration. It is only the following claims, including all equivalents, that are intended to define the scope of this invention.

What is claimed is:

1. A whole blood collection device comprising:
    a reservoir;
    a metering chamber that empties into the reservoir;
    a fill port that empties into the metering chamber; and
    a seal comprising a sweeping element movable between a fill position, in which the seal isolates the reservoir from the metering chamber while allowing fluid flow from the fill port into the metering chamber; an intermediate position, in which the seal isolates the metering chamber from the fill port and from the reservoir; and a closed position, in which the seal isolates the fill port from the metering chamber and allows fluid flow into the reservoir from the metering chamber;
    said reservoir, metering chamber, fill port and seal forming a portable, handheld unit.
2. The invention of claim 1 wherein the seal comprises a first side that faces the fill port and a second side that faces the reservoir and the metering chamber.
3. The invention of claim 1 wherein the metering chamber comprises a capillary channel.
4. The invention of claim 3 further comprising a view port in fluid communication with the capillary channel, said view port spaced from the fill port along the channel.
5. The invention of claim 4 wherein the seal closes the fill port and the view port in the closed position.
6. The invention of claim 1 wherein the sweeping element is sized to fit within the metering chamber, wherein the sweeping element moves along the metering chamber to sweep fluid from the metering chamber to the reservoir as the seal moves from the fill position to the closed position.
7. The invention of claim 6 wherein the fill port is formed in an upper plate, wherein the metering chamber and the reservoir are formed in a lower plate, and wherein the seal is disposed between the upper and lower plates.
8. The invention of claim 6 wherein the seal is mounted for rotation relative to the upper and lower plates about an axis, and wherein the sweeping element and the metering chamber are concentric with the axis.
9. The invention of claim 8 wherein the seal extends over an arc of about 270 degrees and the metering chamber extends over an arc of about 90 degrees.
10. The invention of claim 6 wherein the metering chamber and the sweeping element are arcute in shape.
11. The invention of claim 1 wherein the reservoir comprises a diluting liquid.
12. The invention of claim 11 wherein the metering chamber defines a first volume, and wherein the diluting liquid has a volume at least as great as the first volume.
13. The invention of claim 11 wherein the metering chamber defines a first volume, and wherein the diluting liquid has a volume at least as great as three times the first volume.
14. The invention of claim 11 wherein the metering chamber defines a first volume, and wherein the diluting liquid has a volume at least as great-as six times the first volume.
15. The invention of claim 11 wherein the metering chamber defines a first volume, and wherein the diluting liquid has a volume at least as great as nine times the first volume.
16. The invention of claim 11 wherein the diluting liquid comprises a blood stabilizing composition.
17. The invention of claim 1 further comprising a porous pad disposed between the fill port and the metering chamber, wherein the pad comprises an anticoagulant.
18. The invention of claim 1 wherein the seal closes the fill port in the closed position.
19. The invention of claim 1 wherein the reservoir and the metering chamber are fixedly positioned with respect to one another.
20. The invention of claim 1 wherein the reservoir and the metering chamber remain in a fixed spatial position relative to one another as the seal is moved from the fill position to the closed position.

21. The invention of claim 1 further comprising a snap latch operative to retain the seal in the closed position.

22. A method for collecting a metered sample of a biological sample, said method comprising:
 (a) providing a handheld collection device comprising a reservoir, a metering chamber that empties into the reservoir, and a fill port that empties into the metering chamber, said reservoir containing a diluting liquid;
 (b) filling the metering chamber with a biological sample while isolating the reservoir from the metering chamber;
 (c) sweeping the biological sample from the metering chamber into the reservoir with a sweeping element that moves along the metering chamber to dilute the biological sample with the diluting liquid; and
 (d) sealing the reservoir.

23. The method of claim 22 further comprising:
 (e) providing a stabilizing composition in the diluting liquid.

24. The method of claim 22 wherein the biological sample of (b) comprises whole blood and wherein the method further comprises:
 (e) adding an anticoagulant to the whole blood during (b).

25. The method of claim 22 further comprising:
 (e) shipping the collection device after (d) to a remote site for analysis.

26. The method of claim 22 wherein the biological sample of (b) comprises whole blood.

27. The method of claim 22 or 26 wherein the biological sample swept into the reservoir in (c) is no greater in volume than the diluting liquid in the reservoir.

28. The method of claim 22 or 26 wherein the biological sample swept into the reservoir in (c) is no greater in volume than one-third the volume of the diluting liquid in the reservoir.

29. The method of claim 22 or 26 wherein the biological sample swept into the reservoir in (c) is no greater in volume than one-sixth the volume of the diluting liquid in the reservoir.

30. The method of claim 22 or 26 wherein the biological sample swept into the reservoir in (c) is no greater in volume than one-ninth the volume of the diluting liquid in the reservoir.

31. A whole blood collection device comprising:
 a reservoir;
 a metering chamber that empties into the reservoir;
 a fill port that empties into the metering chamber; and
 a seal movable between a fill position, in which the seal isolates the reservoir from the metering chamber while allowing fluid flow from the fill port into the metering chamber; and a closed position, in which the seal isolates the fill port from the metering chamber and allows fluid flow into the reservoir from the metering chamber;
 wherein the seal comprises a first side that faces the fill port and a second side that faces the reservoir and the metering chamber.

32. A whole blood collection device comprising:
 a reservoir;
 a metering chamber that empties into the reservoir;
 a fill port that empties into the metering chamber; and
 a seal movable between a fill position, in which the seal isolates the reservoir from the metering chamber while allowing fluid flow from the fill port into the metering chamber; and a closed position, in which the seal isolates the fill port from the metering chamber and allows fluid flow into the reservoir from the metering chamber;
 wherein the seal comprises a sweeping element sized to fit within the metering chamber, wherein the sweeping element moves along the metering chamber to sweep fluid from the metering chamber to the reservoir as the seal moves from the ill position to the closed position.

33. A whole blood collection device comprising:
 a reservoir;
 a metering chamber that empties into the reservoir;
 a fill port that empties into the metering chamber; and
 a seal movable between a fill position, in which the seal isolates the reservoir from the metering chamber while allowing fluid flow from the fill port into the metering chamber; and a closed position, in which the seal isolates the fill port from the metering chamber and allows fluid flow into the reservoir from the metering chamber;
 wherein the seal closes the fill port in the closed position.

34. A whole blood collection device comprising:
 a reservoir;
 a metering chamber that empties into the reservoir;
 a fill port that empties into the metering chamber; and
 a seal movable between a fill position, in which the seal isolates the reservoir from the metering chamber while allowing fluid flow from the fill port into the metering chamber; and a closed position, in which the seal isolates the fill port from the metering chamber and allows fluid flow into the reservoir from the metering chamber;
 wherein the metering chamber comprises a capillary channel;
 further comprising a view port in fluid communication with the capillary channel, said view port spaced from the fill port along the channel;
 wherein the seal closes the fill port and the view port in the closed position.

* * * * *